United States Patent [19]

Mosteller

[11] Patent Number: 4,496,346
[45] Date of Patent: Jan. 29, 1985

[54] INFUSION MONITORING APPARATUS
[75] Inventor: Thomas F. Mosteller, Lansdale, Pa.
[73] Assignee: Air-Shields, Inc., Hatboro, Pa.
[21] Appl. No.: 523,870
[22] Filed: Aug. 17, 1983
[51] Int. Cl.³ .............................................. A61M 5/14
[52] U.S. Cl. .................................. 604/123; 604/122; 604/245
[58] Field of Search ................. 604/122, 123, 50, 65, 604/66, 67, 245

[56] References Cited
U.S. PATENT DOCUMENTS

| | | | |
|---|---|---|---|
| 3,935,876 | 2/1976 | Massie et al. | 604/122 X |
| 4,014,206 | 3/1977 | Taylor | 604/122 X |
| 4,280,495 | 7/1981 | Lampert | 604/50 X |
| 4,312,341 | 1/1982 | Zissimopoulos et al. | 604/67 |

Primary Examiner—Edward M. Coven
Attorney, Agent, or Firm—Weiser & Scapler

[57] ABSTRACT

Apparatus for detecting the presence of gas bubbles passing through an infusion tube (10). Sensing means (24, 26) responsive to fluid flow through the infusion tube develop a signal having a characteristic representative of a gas bubble to start a counter (28) which counts timing signals which also drive the pumping means (12, 14, 22) which force infusion liquid through the infusion tube. After a predetermined number of timing signals have been counted corresponding to a gas bubble having a size which may cause injury to a patient being infused, an alarm (30) is actuated.

13 Claims, 2 Drawing Figures

INFUSION MONITORING APPARATUS

DESCRIPTION

1. Technical Field

The present invention relates, in general, to medical infusion apparatus and, in particular, to monitoring equipment for detecting the presence of a gas, most commonly an air bubble, flowing in an infusion tube connected to a patient. As used herein, the term infusion applies both to the introduction of supplementary fluids, such as intravenous medication, intravenous feeding and blood transfusions, and returning body fluids, such as by dialysis and extracorporeal blood circulation.

2. Background Art

A hazard associated with the infusion of liquids into a patient is the presence of gases, most commonly air bubbles, in the liquid. While very small amounts of air, in the order of less than 10 microliters, introduced into the patient will not cause injury, larger amounts of air can create serious medical problems.

Various air bubble detectors have been suggested previously and put into use. Typically, these units include a sensor which monitors the movement of fluid through the infusion tube and can distinguish between the liquid being infused and air. Upon detecting the passage of an air bubble through the tube, the output signal of the sensor changes and such changes in the output signal of the sensor are used to actuate an alarm. Optical sensing is commonly used to detect air bubbles.

Some of the air bubble detectors in use today are conditioned to provide an alarm indication whenever an air bubble is detected, regardless of the size of the air bubble. Others only actuate an alarm when the air bubble exceeds a certain size.

Representative of the latter type of air bubble detector is one in which two sensors are spaced apart a distance corresponding to the maximum air bubble to be passed without the alarm being actuated. Only when both sensors detect air simultaneously is the alarm used. Otherwise, the air bubbles are too small to be detected by the two sensors at the same time and their passage occurs without the system alarming.

This detector suffers from a number of shortcomings. First, two small air bubbles, spaced apart the same distance as the sensors, can appear as one large bubble because both sensors detect an air bubble at the same time. Second, it is difficult to position the sensors precisely to establish the alarm threshold because the overall bubble sizes are relatively small. As a result, this detector is not arranged for conveniently varying the threshold of acceptable sizes of air bubbles for passage without issuing the alarm as may be desirable for different patients being treated in different ways.

DISCLOSURE OF THE INVENTION

Accordingly, it is an objective of the present invention to provide new and improved infusion apparatus.

It is another objective of the present invention to provide infusion monitoring apparatus which detects the presence of air bubbles of a certain size or greater in the liquid being infused into a patient.

It is further objective of the present invention to provide infusion monitoring apparatus which is relatively simple in construction and inexpensive to fabricate.

Infusion apparatus, constructed in accordance with the present invention, includes an infusion tube for conducting liquid and sensing means responsive to fluid flow through the infusion tube for sensing the presence of gas bubbles in the liquid and for developing a control signal having a first characteristic representative of liquid flow through the infusion tube and a second characteristic representative of a gas bubble flowing through the infusion tube. Also included are timing means for developing a series of timing signals having a rate proportional to the rate of fluid flow through said infusions tube and counting means responsive to the second characteristic of the control signal and the timing signals for counting the timing signals during the presence of a gas bubble and for developing an alarm signal after a predetermined number of timing signals have been counted. The infusion apparatus also includes alarm means responsive to the alarm signal for developing an alarm. In the preferred form of the invention, the pumping means which force prescribed amounts of liquid through the infusion tube at prescribed times are synchronized with the timing signals.

BRIEF DESCRIPTION OF THE DRAWING

Referring to the drawing.

BEST MODE OF CARRYING OUT THE INVENTION

Figure 1:
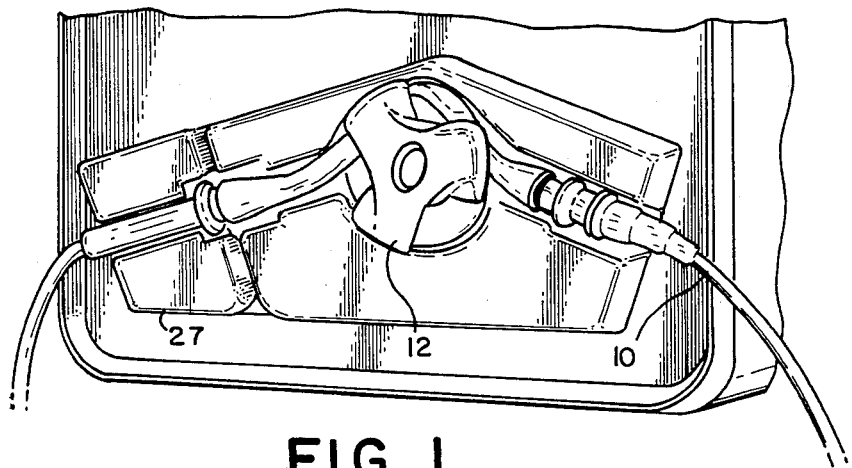
FIG. 1 is a front view of infusion apparatus incorporating the present invention.
Figure 2:
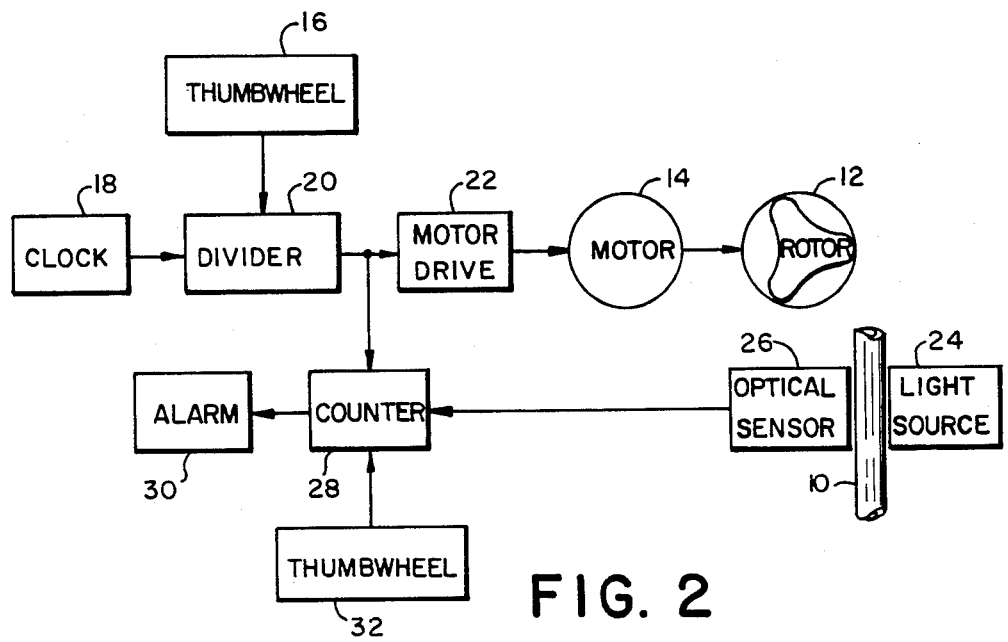
FIG. 2 is a block diagram of infusion monitoring apparatus constructed in accordance with the present invention.

Referring to FIGS. 1 and 2, infusion apparatus constructed in accordance with the present invention includes an infusion tube 10 for conducting liquid. Tube 10 may be made from a suitable silicone material. It may be connected at one end to a source of the liquid to be infused into a patient and have at its other end the usual components for introducing the liquid into a patient.

Prescribed amounts of liquid are forced through infusion tube 10 by means of a rotor 12 driven by a motor 14. Various rotors may be used. The one described, illustrated and claimed in copending U.S. application Ser. No. 353,042 filed on Mar. 1, 1982 and assigned to the same assignee as this application is preferred and the contents of U.S. application Ser. No. 353,042 are incorporated by reference.

Motor 14 preferably is a conventional stepping motor which causes rotor 12 to undergo incremental movements to repetitively pump prescribed amounts of liquid through infusion tube 10. The speed of motor 14 is established by the setting of a control member, such as a thumbwheel 16, located at a convenient place on the housing of the apparatus. Thumbwheel 16 is set so that rotor 12 causes the desired amounts of infusion liquid to be delivered to the patient.

A free-running clock 18, of conventional construction and operation, supplies a series of clock signals to a divider 20, also of conventional construction and operation. The operation of divider 20 is controlled by the setting of thumbwheel 16. The output of divider 20 is a series of timing signals which are supplied to a motor drive 22 for powering motor 14 to turn at the speed required to deliver the desired amounts of infusion liquid to the patient.

The infusion monitoring apparatus of the present invention also includes sensing means responsive to fluid flow through infusion tube 10 for sensing the presence of a gas bubbles in the liquid being pumped through the infusion tube. The sensing means may include a light source 24 and an optical sensor 26 located in a housing 27 positioned on opposite sides of infusion tube 10 downstream from rotor 12. Light source 24 may be a conventional infra-red source and optical sensor 26 may be a conventional detector which, upon receiving the infra-red light propagated by light source 24, develops a control signal dependent upon the nature of the medium passing through infusion tube 10 between the light source and the sensor. Specifically, the control signal developed by optical sensor 26 has a first level so long as liquid is flowing through infusion tube 10 and a second level when an air bubble is flowing through the infusion tube. The transmission characteristics and index of refraction of air relative to the transmission characteristics and index of refraction of infusion liquid cause the level of control signal to drop representative of the passage of an air bubble through the infusion tube.

The infusion monitoring apparatus of the present invention further includes counting means responsive to the control signal developed by optical sensor 26 and the timing signals supplied by divider 20 for counting the timing signals during the presence of an air bubble in infusion tube 10. Such counting means may be in the form of a counter 28 which commences counting timing signals whenever the level of the control signal drops representing the passage of an air bubble. Counter 28 is reset whenever the level of the control signal rises and returns to the level representing the flow of infusion liquid.

By synchronizing counter 28 and motor 14, the number of timing signals counted by counter 28 represents the size of an air bubble passing through the infusion tube 10 in that the rate is proportional to the linear velocity of the air bubbles because each step of the motor moves the same amount of air through the infusion tube. After a predetermined number of timing signals, representative of the maximum acceptable air bubble, have been counted, counter 28 develops an alarm signal which actuates a suitable alarm 30.

Infusion monitoring apparatus, constructed in accordance with the present invention, may be arranged to alarm at different bubble sizes. This may be accomplished by a control member, such as a thumbwheel 32, which controls counter 28 to establish the number of counts required to develop the alarm signal.

While in the foregoing there has been described a preferred embodiment of the present invention, it should be understood to those skilled in the art that various modifications and changes can be made without departing from the true spirit and scope of the invention as recited in the claims.

What is claimed is:
1. Infusion monitoring apparatus comprising:
an infusion tube for conducting liquid;
sensing means responsive to fluid flow through said infusion tube for sensing the presence of gas bubbles in said liquid and for developing a control signal having a first characteristic representative of liquid flow through said infusion tube and a second characteristic representative of a gas bubble flowing through said infusion tube;
timing means for developing a series of timing signals having a rate proportional to the rate of fluid flow through said infusion tube;

counting means responsive to said second characteristic of said control signal and said timing signals for counting said timing signals during the presence of a gas bubble and for developing an alarm signal after a predetermined number of said timing signals have been counted;
and an alarm means responsive to said alarm signal for developing an alarm.

2. Infusion monitoring apparatus according to claim 1 further including means for repetitively pumping prescribed amounts of liquid through said infusion tube.

3. Infusion monitoring apparatus according to claim 2 wherein said timing signals drive said pumping means.

4. Infusion monitoring apparatus according to claim 3 wherein said sensing means include a light source and an optical sensor positioned on opposite sides of said infusion tube.

5. Infusion pumping apparatus according to claim 2 wherein said counting means include means for varying the number of timing signals required to develop said alarm signal.

6. Infusion apparatus comprising:
an infusion tube for conducting liquid;
sensing means responsive to fluid flow through said infusion tube for sensing the presence of gas bubbles in said liquid and for developing a control signal having a first characteristic representative of liquid flow through said infusion tube and a second characteristic representative of a gas bubble flowing through said infusion tube;
timing means for developing a series of timing signals;
pumping means responsive to said timing signals for forcing prescribed amounts of liquid through said infusion tube at prescribed times corresponding to the occurrence of said timing signals;
counting means responsive to said second characteristic of said control signal and said timing signals for counting said timing signals during the presence of a gas bubble and for developing an alarm signal after a predetermined number of said timing signals have been counted;
and alarm means responsive to said alarm signal for developing an alarm.

7. Infusion apparatus according to claim 6 wherein said timing means include:
(a) a free-running clock for supplying a series of clock signals at a selected rate;
(b) control means for establishing the rate at which said pumping means will force infusion liquid through said infusion tube; and
(c) means responsive to said free-running clock and said control means for developing said timing signals.

8. Infusion apparatus according to claim 7 wherein said pumping means include:
(a) a stepping motor responsive to said timing signals; and
(b) a rotor driven by said stepping motor for forcing liquid through said infusion tube during the occurrence of said timing signals.

9. Infusion apparatus according to claim 8 wherein said sensing means include a light source and an optical sensor positioned on opposite sides of said infusion tube.

10. Infusion apparatus according to claim 9 wherein said light source is an infra-red light source.

11. Infusion apparatus according to claim 6 wherein said counting means commence counting said timing signals in response to said second characteristic of said control signal and said counting means are reset in response to said first characteristic of said control signal.

12. Infusion apparatus according to claim 11 wherein said first characteristic of said control signal is one level of said control signal and said second characteristic of said control signal is a lower level of said control signal.

13. Infusion pumping apparatus according to claim 6 wherein said counting means include means for varying the number of timing signals required to develop said alarm signal.

* * * * *